United States Patent [19]
Shim

[11] B 3,992,489
[45] *Nov. 16, 1976

[54] POLYALKYLENE GLYCOL VINYL PHOSPHATES

[75] Inventor: Kyung S. Shim, Irvington, N.Y.

[73] Assignee: Stauffer Chemical Company, Westport, Conn.

[ * ] Notice: The portion of the term of this patent subsequent to June 25, 1991, has been disclaimed.

[22] Filed: Sept. 6, 1974

[21] Appl. No.: 502,993

[44] Published under the second Trial Voluntary Protest Program on February 17, 1976 as document No. B 502,993.

Related U.S. Application Data

[63] Continuation-in-part of Ser. No. 389,607, Aug. 20, 1973, abandoned, which is a continuation-in-part of Ser. No. 63,262, Aug. 6, 1970, abandoned.

[52] U.S. Cl. .......................... 260/929; 260/2.5 AJ; 260/2.5 AR; 260/969
[51] Int. Cl.² ...................... C07F 9/11; C08J 9/00
[58] Field of Search ........................... 260/969, 929

[56] References Cited
UNITED STATES PATENTS
3,819,750   6/1974   Shim .................................. 260/929

Primary Examiner—Anton H. Sutto
Attorney, Agent, or Firm—Richard P. Fennely

[57] ABSTRACT

Polyalkylene glycol vinyl phosphates having the formula:

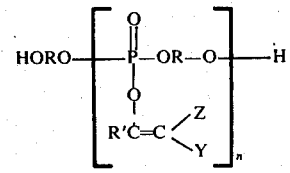

where R is a polyalkylene glycol residue, $n$ is an integer from 1 to about 100, R' is either hydrogen, alkyl or haloalkyl, and Z and Y are each either halogen, hydrogen or alkyl are produced by transesterifying a tertiary phosphite with a polyalkylene glycol and reacting the product thereof with a carbonyl compound.

7 Claims, No Drawings

3,992,489

POLYALKYLENE GLYCOL VINYL PHOSPHATES

RELATED APPLICATION

This application is a continuation-in-part of U.S. application Ser. No. 389,607, filed Aug. 20, 1973, now abandoned, which in turn is a continuation-in-part of U.S. application Ser. No. 63,262, filed Aug. 6, 1970 by Kyung Sup Shim now abandoned.

BACKGROUND OF THE INVENTION

In the polyurethane filed, increased interest is being shown in compounds which can be added to the polyurethane polymers to act as fire retardant agents. Particular interest is being shown in compounds which have functional groups reactive with the polyol or polyisocyanate used in preparing the polyurethane so that the fire retardant agent can be copolymerized into the polymer chain. One such group of compounds of this type are the polyalkylene glycol polyphosphites and phosphonates. In general, these materials are prepared by transesterifying a secondary phosphite with a polyalkylene glycol in the presence of an alkaline catalyst such as sodium or sodium methylate. However, many of these materials have relatively high acidity causing them to react with and thereby deactivate certain catalyst systems generally used in the formation of polyurethane polymers such, for example, as tertiary amine compounds. To alleviate this problem, the polyalkylene glycol phosphonates have heretofore been reacted with materials such as alkylene oxides in order to reduce the number of acid groups on the phosphorus. However, addition of the alkylene groups onto the phosphorus has decreased the relative flame retardancy of these compounds. Alternatively, secondary polyalkylene glycol phosphites have been reacted with carbon tetrachloride or chloral in order to add flame retardant chlorine atoms to the molecule. However, the phosphonates formed in this manner are still relatively high in acidity.

Therefore, it is an object of the present invention to produce a class of compounds which are compatible with polyurethane foams, which can be copolymerized therewith, which have a high degree of flame retardancy and which are relatively low in acidity. Various other objects and advantages of this invention will be apparent from a reading of the disclosure which follows hereinafter.

TECHNICAL DESCRIPTION OF THE INVENTION

It has now been discovered that this object can be realized by employing novel polyalkylene glycol vinyl phosphates, produced by transesterifying a tertiary phosphite with a polyalkylene glycol, and reacting the polyphosphite so obtained with a carbonyl compound. The novel compounds of the present invention have a formula corresponding to:

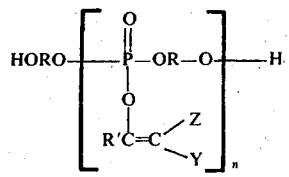

wherein $n$ is a number having a value of from 1 to about 100, Y and Z are each selected from the group consisting of hydrogen, halogen or alkyl, having from 1 to about 4 carbon atoms, R is a polyalkylene glycol residue and R' is hydrogen, alkyl or haloalkyl having from 1 to 4 carbon atoms, provided Z and Y are not both hydrogen or alkyl.

The term polyalkylene glycol residue is meant to designate that portion remaining after two hydroxyl groups have been removed from a polyalkylene glycol having the formula:

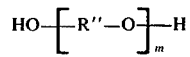

wherein R'' is an alkylene group of from 2 to about 20 carbon atoms, and m designates the number of repeating alkylene ether units and is normally from 2 to about 20.

Illustrative of the compounds of the present invention are the following:
tripropylene glycol-$\beta,\beta$-dichlorovinyl phosphate
bis(tripropylene glycol-$\beta,\beta$-dichlorovinyl phosphate)
tris(tripropylene glycol-$\beta,\beta$-dichlorovinyl phosphate)
poly(tripropylene glycol-$\beta,\beta$-dichlorovinyl phosphate)
dipropylene glycol-$\beta,\beta$-dichlorovinyl phosphate
bis(dipropylene glycol-$\beta,\beta$-dichlorovinyl phosphate)
tris(dipropylene glycol-$\beta,\beta$-dichlorovinyl phosphate)
poly(dipropylene glycol-$\beta,\beta$-dichlorovinyl phosphate)
triethylene glycol-$\beta,\beta$-dichlorovinyl phosphate
bis(triethylene glycol-$\beta,\beta$-dichlorovinyl phosphate)
poly(triethylene glycol-$\beta,\beta$-dichlorovinyl phosphate)
tributylene glycol-$\beta,\beta$-dichlorovinyl phosphate
bis(tributylene glycol-$\beta,\beta$-dichlorovinyl phosphate)
tris(tributylene glycol-$\beta,\beta$-dichlorovinyl phosphate)
tris(triethylene glycol-$\beta,\beta$-dichlorovinyl phosphate)
poly(tributylene glycol-$\beta,\beta$-dichlorovinyl phosphate)
dibutylene glycol-$\beta,\beta$-dichlorovinyl phosphate
bis(dibutylene glycol-$\beta,\beta$-dichlorovinyl phosphate)
tris(dibutylene glycol-$\beta,\beta$-dichlorovinyl phosphate)
poly(dibutylene glycol-$\beta,\beta$-dichlorovinyl phosphate)
trihexylene glycol-$\beta,\beta$-dichlorovinyl phosphate
bis(trihexylene glycol-$\beta,\beta$-dichlorovinyl phosphate)
tris(trihexylene glycol-$\beta,\beta$-dichlorovinyl phosphate)
poly(trihexylene glycol-$\beta,\beta$-dichlorovinyl phosphate)
tripropylene glycol-$\beta,\beta$-dibromovinyl phosphate
bis(tripropylene glycol-$\beta,\beta$-dibromovinyl phosphate)
tris(tripropylene glycol-$\beta,\beta$-dibromovinyl phosphate)
poly(tripropylene glycol-$\beta,\beta$-dibromovinyl phosphate)
dipropylene glycol-$\beta,\beta$-dibromovinyl phosphate
poly(dipropylene glycol-$\beta,\beta$-dibromovinyl phosphate)
poly(triethylene glycol-$\beta,\beta$-dibromovinyl phosphate)
poly(dibutylene glycol-$\beta,\beta$-dibromovinyl phosphate)
poly(tributylene glycol-$\beta,\beta$-dibromovinyl phosphate)
poly(trihexylene glycol-$\beta,\beta$-dibromovinyl phosphate)
the monomer, dimer, trimer, and higher polymer of a polypropylene glycol-$\beta,\beta$-dichlorovinyl and dibromovinyl phosphates wherein the polypropylene glycol has an average of 14 ether units; the monomer, dimer, trimer and higher polymer of a polyethylene glycol-$\beta,\beta$-dichlorovinyl and dibromovinyl phosphates wherein the polyethylene glycol has an average of 2 ether units, poly(dipropylene glycol-$\alpha$-methyl-$\beta,\beta$-dichlorovinyl phosphate), poly(tripropylene glycol-$\alpha$-methyl-$\beta,\beta$-dichlorovinyl phosphate), poly(tributylene glycol-$\alpha$-methyl-$\beta,\beta$-dichlorovinyl phosphate), poly(-tripropylene glycol-$\alpha$-trichloromethyl-$\beta,\beta$-dichlorovinyl phosphate), poly(dipropylene glycol-α-methyl-β,β-dibromovinyl phosphate), poly(tripropylene glycol-α-methyl-β,β-dibromovinyl phosphate), mixtures thereof and the like. It is understood that the compounds of the present invention are usually obtained as mixtures of the monomer, dimer, trimer and polymer rather than as the pure monomer. However, these mixtures perform as well in the urethane foams as the unmixed monomer.

In accordance with the present invention, a tertiary phosphate is initially reacted with a polyalkylene glycol to yield the intermediate polyalkylene glycol phosphite. The term tertiary phosphite as used herein is meant to designate compounds having the formula:

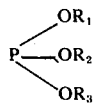

wherein $R_1$, $R_2$ and $R_3$ are each alkyl having from 1 to about 10 carbon atoms or aryl. Illustrative of the alkyl groups are methyl, ethyl, propyl, butyl, hexyl and the like. The term alkyl is also intended to include substituted alkyl groups, including aromatic substituted alkyls such as benzyl and the like. Illustrative of the aryl groups are phenyl and naphthyl groups and substituted forms thereof. The tertiary phosphites which are preferred for use in the present invention are trimethyl phosphite, triethyl phosphite, triisopropyl phosphite, tributyl phosphite, triphenyl phosphite, dimethyl ethyl phosphite, and methyl diethyl phosphite.

The selected tertiary phosphite is transesterified with a polyalkylene glycol. The term polyalkylene glycol as used herein is meant to designate those compounds having a formula corresponding to:

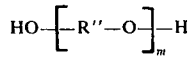

wherein R'' and m are as defined above. Illustrative of the polyalkylene glycols which can be employed in the present invention are: diethylene glycol, triethylene glycol, dipropylene glycol, tripropylene glycol, dibutylene glycol, tributylene glycol, polyethylene glycols where the average number of ether units is 2, polypropylene glycols where the average number of ether units is 14, trihexylene glycol and the like.

The transesterification step is accomplished by reacting the tertiary phosphite with the polyalkylene glycol in approximately a 1:1 molar ratio. By employing this equimolar proportion of reactants, polyalkylene phosphites having the formula:

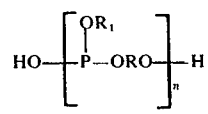

wherein $R_1$, R and n are as defined above, are obtained. The temperature at which the transesterification step is conducted is from about 80° C. to about 200° C. and preferably at from about 100° C. to about 150° C.

This reaction can be improved by employing any of the well known transesterification catalysts. Particularly useful catalysts are the alkali metal alcoholates and phenolates such as sodium methylate, sodium phenolate, sodium decylate and the like. These catalysts are normally employed in an amount from 0.01 to 5 percent, by weight, of the entire reactant mixture. The degree of transesterification can be measured by the quantity of by-product alcohol formed. For example, when 1 mole of trimethyl phosphite is reacted with 1 mole of tripropylene glycol, the transesterification is completed when 2 moles of methanol has been evolved. The reaction time will vary over a wide range depending upon the reactants, temperature and catalyst used. Normally reaction times will be in the range from about 0.5 to 50 hours.

The polyalkylene phosphonate produced by the transesterification step is then reacted with a carbonyl compound having the formula:

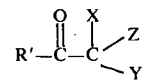

where R', Z and Y are as defined above with the proviso that the carbonyl compound is one which does not have monohalosubstitution on an alpha carbon atoms and X is bromine or chlorine. Z and Y cannot both be hydrogen or alkyl. These carbonyl compounds can be illustrated by the following: chloral, bromal, 1,1,1-trichloroacetone, 1,1,1-tribromoacetone, hexachloroacetone, dichloroacetaldehyde, dibromoacetaldehyde, dichloromethyl ethyl ketone, trichloromethyl ethyl ketone, and the like. Particularly preferred compounds for use in the present invention are chloral, bromal, dichloroacetaldehyde and dibromoacetaldehyde.

The carbonyl compounds defined above are normally reacted with the transesterification product in approximately equimolar proportions with respect to the starting tertiary phosphite. The reaction is conducted at a temperature in the range from about 0° to about 100°C., and, preferably, at from about 10° to about 40°C. The reaction can be monitored by determining the amount of alkyl or aryl chloride by-product formed. The reaction is complete when approximately 1 mole of chloride has been formed for each mole of carbonyl compound employed.

Both the transesterification and the subsequent reaction with the carbonyl compound can, if desired, be carried out in the presence of a solvent or diluent although this is not necessary to the invention. The solvent or diluent should be non-reactive with respect to both the starting materials and the desired products, and should be miscible therewith. The solvent can also form an azeotrope with the by-product alkanol or phenol of the transesterification step. Illustrative of suitable solvents are benzene, xylene, ethylbenzene, diethylbenzene, various alkanes having boiling points greater than that of the by-product, and the like.

The novel compounds of the present invention are characterized by their ability to copolymerize with polyisocyanates employed in forming polyurethanes and by their relatively low acidity. These compounds can completely replace the polyols normally employed in forming the foams or they may be used in combination with the polyols, thereby yielding foams with greatly improved flame resistance. The acid numbers of the compounds of the present invention are normally below about 2 mg. of KOH per gram of the polyalkylene glycol vinyl phosphates. This low acidity makes these compounds relatively unreactive toward the polymerization catalysts employed in producing the polyurethane foams. The high percentage of the flame retardant phosphorus and chlorine atoms present in these compounds reduces the concentration necessary to achieve a flame resistant foam.

A further advantage of the compounds of the present invention is their ability to render the foam self-extinguishing. This characteristic is particularly important in the area of flexible urethane foams. Normally the compounds of the present invention can be employed in amounts of from about 5 to about 30 percent, by weight, of foam to yield self-extinguishing flexible foams. The amount will vary depending upon the particular foam used.

The novel compounds of the present invention can also be used as flame retardants in a wide variety of polymeric systems. Illustrative of these systems are: polyesters, polyolefins, cellulose ethers and esters, urethane coatings and elastomers, polymethyl methacrylates, polyvinyl chlorides and many others. These compounds can also be employed in combination with any of the known flame retardants and can also be used as the sole flame retardant foams or polymers.

The present invention will be further illustrated by the following examples:

EXAMPLE 1

To a 500 ml. flask fitted with a thermometer, mechanical stirrer and distilling head was charged 402 grams (3 moles) of dipropylene glycol, 372 grams (3 moles) of trimethyl phosphite and 1.5 grams of sodium methylate under a nitrogen atmosphere. The mixture was heated to 110° C. and maintained at this temperature for 8 hours. Then, pressure was reduced by water aspiration to approximately 15 millimeters of Hg and the temperature was kept at 100° C. for another hour. The resulting mixture was cooled in an ice bath and the distilling head was replaced with a dropping funnel containing 442.5 grams (3 moles) of chloral. The chloral was added dropwise while maintaining the temperature below 30° C. by means of an ice bath. The mixture was then allowed to stand at room temperature overnight. The volatiles were removed from the product at 50° C. and 0.3 mm. pressure, leaving 886 grams of a viscous clear oil (98% yield). An infrared analysis revealed vinyl stretching frequency at $1630^{-1}$ cm. Analysis of the product confirmed the structure to be poly(-dipropylene glycol-$\beta,\beta$-dichlorovinyl phosphate) having an average n value of 6. In addition, it had an acid number of 0.1 milligram of KOH/gram of product.

EXAMPLE 2

Employing the method of Example 1, 192 grams (1 mole) of tripropylene glycol was reacted with 124 grams (1 mole) of trimethyl phosphite in the presence of 0.5 grams of sodium methylate. After removal of the methanol, 147.4 grams (1 mole) of chloral was added. Again, the temperature was maintained below 30° C. during the addition of the chloral. Isolation of the product yielded 475 grams was 99.5 percent of theoretical. The acid number of the product was 1.4 mg. KOH/g sample. The product was shown by I.R. and Elemental Analysis to be poly(tripropylene glycol-$\beta,\beta$-dichlorovinyl phosphate) having an average $n$ value of 5.

EXAMPLE 3

106 grams (1 mole) of diethylene glycol was reacted with 124 grams (1 mole) of trimethyl phosphate in the presence of 0.37 grams of sodium methylate according to the procedure of Example 1. To the resulting reaction product was added 100 ml. of benzene and this mixture was then cooled by means of an ice bath. A mixture of 100 ml. of benzene and 147.4 grams (1 mole) of chloral was then added dropwise to the reaction product mixture while maintaining the temperature below 30° C. This mixture was then stirred overnight at room temperature. The benzene and other volatiles were then removed at 80° C. under reduced pressure. The product was a light yellow viscous oil having an acid number of 1.31. The product was analyzed and shown to be poly(diethylene glycol-$\beta,\beta$-dichlorovinyl phosphate) having an average n value of 7.

EXAMPLE 4

268 grams (2 moles) of dipropylene glycol was reacted with 248 grams (2 moles) of trimethyl phosphite in the presence of 0.75 grams of sodium methoxide according to the procedures of Example 1. To the reaction product was added, with stirring, 500 ml. of benzene and this mixture was stirred overnight at room temperature. Next, 323 grams (2 moles) of trichloroacetone was added dropwise to the benzene reaction mixture over a period of 3 hours while maintaining the temperature in the range from about 15 to about 25° C. After the product had been allowed to sit at room temperature overnight, it was heated to 50° C. for 4 hours. An aspirator was used to reduce the pressure and the volatile components were removed at 50° C. yielding a colorless oil in a product yield of 90% of the theoretical yield. The product had an acid number of 1.53 and analysis showed it to be poly(dipropylene glycol-$\alpha$-methyl-$\beta,\beta$-dichlorovinyl phosphate) having an average n value of 6.

EXAMPLE 5

33.5 grams (0.25 moles) of dipropylene glycol was reacted with 31.0 grams (0.25 moles) of trimethyl phosphite according to the procedure of Example 1. 100 ml. of benzene was added and the temperature of the reactant mixture was lowered to 10° C. by means of an ice bath. Next, 70.3 grams (0.25 moles) of bromal was added dropwise over a period of 75 minutes, while maintaining the temperature at 10° C. After completion of the addition, the reactant mixture was allowed to come up to room temperature and stirred for several hours. The temperature was then raised to 50° C. for another hour and a half. Stripping off the volatiles at 65° C. followed by aspiration at reduced pressure, then at high vacuum, yielded 93.5 grams of a dark brown viscous oil. Analysis showed this to be poly(dipropylene glycol-$\beta,\beta$-dibromovinyl phosphate.

EXAMPLE 6

Employing the procedure of Example 1, 536 grams (4 moles) of dipropylene glycol was reacted with 496 grams (4 moles) of trimethyl phosphite in the presence of 1.5 grams of sodium methoxide, and the resulting reaction product was then reacted with 588 grams (4 moles) of chloral in 500 ml. of benzene. The product was a light yellow oil having an acid number of 0.93 milligrams of KOH/gram of product. This product was then incorporated into a foam formulation as set forth in Table 1.

TABLE I

| | Grams |
|---|---|
| Polyol, (3000 M.W. triol, propoxylated glycerol (ethylene oxide-capped) | 100 |
| The compound of Example 6 | 30 |
| Silicone sulfactant | 1.0 |
| Water | 3.9 |
| Dimethyl ethanolamine (DMEA) | 0.30 |
| 1-(N,N-dimethylaminoethyl)-4-methylpiperazine | 0.10 |
| Methylene chloride | 3.0 |
| Stannous octoate, 50% solution in dioctyl phthalate | 0.60 |

Upon addition of 52.9 g. of toluene diisocyanate (80%, 2,4 and 20%, 2,6 isomers), this mixture yielded a flexible urethane foam with good physical and flame retardancy properties. The foam was self-extinguishing and exhibited no differences in physical properties when compared with a similar foam formulated without the compound of Example 6.

What is claimed is:

1. Polyalkylene glycol vinyl phosphates having the formula:

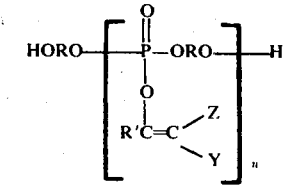

where R is a polyalkylene glycol residue obtained by removing two hydroxyl groups from a polyalkylene glycol having the formula

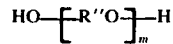

where $R''$ is an alkylene group of from 2 to about 20 carbon atoms, and m is from 2 to about 20, $n$ is an integer from 1 to about 100, $R'$ is selected from the group consisting of hydrogen, alkyl and haloalkyl, Z and Y are each selected from the group consisting of halogen, hydrogen and alkyl, provided Z and Y are not both hydrogen or alkyl.

2. A composition according to claim 1 within is a tripropylene glycol residue.

3. A composition according to claim 1 wherein R is a triethylene glycol residue.

4. A composition according to claim 1 wherein Y and Z are selected from the group consisting of chlorine and bromine.

5. A composition according to claim 4 wherein $R'$ is hydrogen.

6. A composition according to claim 5 wherein R is a tripropylene glycol residue.

7. A composition according to claim 5 wherein R is a dipropylene glycol residue.

* * * * *